United States Patent [19]

Vigano' et al.

[11] Patent Number: 6,066,741
[45] Date of Patent: *May 23, 2000

[54] PROCESS FOR THE PREPARATION OF ETODOLAC

[75] Inventors: Enrico Vigano', Lurago D'Erba; Paolo Colombo, Castellanza, both of Italy

[73] Assignee: A.M.S.A. Anonima Materie Sintetiche & Affini S.p.A., Italy

[ * ] Notice: This patent issued on a continued prosecution application filed under 37 CFR 1.53(d), and is subject to the twenty year patent term provisions of 35 U.S.C. 154(a)(2).

[21] Appl. No.: 09/149,738

[22] Filed: Sep. 8, 1998

[51] Int. Cl.$^7$ .............................................. C07D 491/052
[52] U.S. Cl. ................................................ 548/432
[58] Field of Search ............................................. 548/432

[56] References Cited

U.S. PATENT DOCUMENTS 3,843,681  10/1974  Demerson et al. ................. 260/326.14
4,309,348  1/1982  Asselin et al. ..................... 260/326.28
4,585,877  4/1986  Demerson et al. ..................... 548/432

OTHER PUBLICATIONS

Costa, et al., Asymetric Friedel–Crafts Reaction . . . , Tetrahedron Letters, 38 (40) 7021–7024, Aug. 1997.

*Primary Examiner*—Joseph McKane
*Assistant Examiner*—Dominic Keating
*Attorney, Agent, or Firm*—Hedman, Gibson & Costigan, P.C.

[57] ABSTRACT

Process for the preparation of etodolac, comprising the following steps:
a) reacting 7-ethyl-tryptophol of formula (II) with methyl 3-oxo-pentanoate of formula (III) thereby obtaining methyl 1,8-diethyl-1,3,4,9-tetrahydropyrano [3,4-bis] indole-1-acetate of formula (IV) in an apolar solvent;
b) hydrolyzing the compound of formula (IV) to etodolac (I), wherein step (a) is carried out at a temperatures of between −20° C. and +50° C. in the presence of a concentrated mineral acid, the molar ratio of the inorganic acid to 7-ethyl-tryptophol being comprised between 0.5 and 5.

9 Claims, No Drawings

PROCESS FOR THE PREPARATION OF ETODOLAC

FIELD OF THE INVENTION

The present invention regards a process for the preparation of etodolac.

STATE OF THE ART 1,8-diethyl-1,3,4,9-tetrahydropyrano[3,4-bis]indole-1-acetic acid, better known with the common name etodolac, is an active principle having high anti-inflammatory activity. In U.S. Pat. No. 3,843,681 compounds are described that are analogues of etodolac and fall within the following general formula (A):

(A)
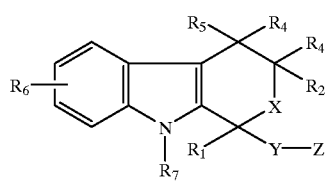

in which $R^1$ is H, a lower alkyl, lower alkenyl, lower cyclo-alkyl, phenyl, benzyl, or thienyl; $R^2$, $R^3$, $R^4$, and $R^5$, which may be the same or different from each other, are H or a lower alkyl; $R^6$, is a lower alkyl, lower cyclo-alkyl, hydroxy, alkoxy, benzyloxy, alkanoyloxy, phenyl, nitro, halogen, mercapto, alkylthio, trifluoromethyl, amino, or sulphamoyl; $R^7$ is H, a lower alkyl, or lower alkenyl; X is O or S; Y is —CO—, —$CR^8(R^9)$—$CR^{10}(R^{11})$—CO—, —$CR^8(R^9)$—$CR^{10}(R^{11})CR^{12}(R^{13})$—CO—, in which $R^8$, $R^9$, $R^{10}$, $R^{11}$, $R^{12}$ and $R^3$, which are the same or different from each other, are H or a lower alkyl; Z is OH, a lower alkoxy, a lower alkylamino, or a lower dialkylamino. These products, and in particular those in which X=O and Z=OH (and therefore etodolac falls within this definition), are prepared by means of condensation of the indole derivative having the following formula (B):

(B)
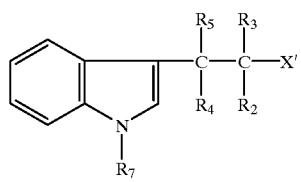

in which $R^2$, $R^3$, $R^4$, $R^5$, $R^6$, and $R^7$ have the meanings indicated above and X' is a hydroxy, with a B-keto ester of formula $R^1$—CO—Y—Z, in which Y has the aforesaid meanings and Z is a lower alkoxy in an apolar solvent, such as benzene or toluene, in the presence of catalytic quantities of para-toluenesulphonic acid, under reflux for a period of time ranging between half an hour and several hours. The patent U.S. Pat. No. 4,585,877 describes an improved process for the specific preparation of etodolac as compared to the process described in the foregoing patent, since the condensation of the tetrahydropyran ring on the indole derivative (7-ethyl-tryptophol in the specific case regarding the preparation of etodolac) is carried our at room temperature and no longer under reflux, using, instead of B-keto ester (the methyl 3-oxo-pentanoate in the specific case of etodolac), the corresponding protected form, i.e., the enol ether of formula (C):

(C)
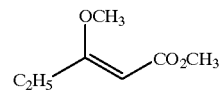

in the presence of $BF_3.Et_2O$ in anhydrous methylene chloride at room temperature. However, the use of catalysts, such as boron trifluoride etherate for industrial production processes causes considerable problems on account of its notable toxicity, and hence for disposal of waste liquor. In addition, this type of catalyst is stable only in a perfectly anhydrous environment, and it is thus difficult to manage.

TECHNICAL PROBLEM

The need is felt for having available an alternative process for the preparation of etodolac which does not involve the drawbacks presented by the processes of the known art.

SUMMARY OF INVENTION

The applicant has now surprisingly found a process for the preparation of etodolac which does not present the drawbacks of the known art in so far it is conducted at lower temperatures than the reflux temperature of the solvent and in the absence of $BF_3.Et_2O$.

This process, which comprises:

a) reacting 7-ethyl-tryptophol of formula (II)

(II)
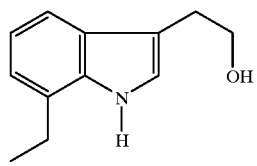

with methyl 3-oxo-pentanoate of formula (III)

(III)
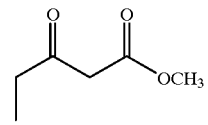

in an apolar solvent thereby obtaining methyl 1,8-diethyl-1,3,4,9-tetrahydropyrano [3,4-bis]indole-1-acetate of formula (IV)

(IV)
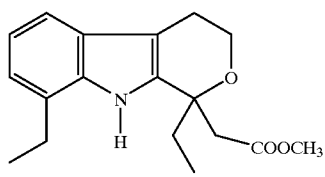

and b) subsequently hydrolysing the intermediate product of formula (IV) to etodolac (I)

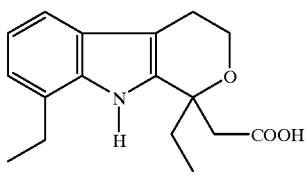

(I)

wherein step (a) is carried out in the presence of high quantities of a concentrated mineral acid, the molar ratio of the inorganic acid to 7-ethyl-tryptophol being comprised between 0.5 and 5, and at a temperature of between −20° C. and +50° C.

DETAILED DESCRIPTION OF THE INVENTION

The inorganic mineral acid used in the process according to the present invention is any acid, such as hydrochloric acid, hydrobromic acid, sulphuric acid, phosphoric or polyphosphoric acid. Preferably, gaseous hydrochloric acid is used dissolved in a $C_1$–$C_5$ alcohol, or concentrated sulphuric acid is used. According to a preferred solution, the alcohol in which the gaseous hydrochloric acid is dissolved is isobutanol. According to a particularly preferred solution, the concentration of the hydrochloric acid in isobutyl alcohol is 20% by weight. The hydrochloric acid is preferably present in a molar ratio of 3:1 with respect to 7-ethyl tryptophol.

Also when the reaction is conducted in the presence of sulphuric acid, isobutanol is preferably added as co-solvent. The sulphuric acid is preferably present in a molar ratio of 3:1 with respect to 7-ethyl tryptophol.

The reaction solvent of step (a) is generally an aromatic hydrocarbon; preferably, toluene is used.

The reaction temperature is preferably kept at 0° C.

The hydrolysis of methyl 1,8-diethyl-1,3,4,9-tetrahydropyrano[3,4-bis]indole-1-acetate (IV) is conducted with conventional methods, such as by addition of aqueous potassium hydroxide to a methanol solution of the above-mentioned intermediate (IV).

7-ethyl tryptophol, i.e., the compound of formula (II) of the process according to the present invention, is prepared according to conventional methods, such as by reaction of 2,3-dihydrofuran with the phenylhydrazine hydrochloride in dioxane at 95° C.

The following examples are given to provide non-limiting illustrations of the process according to the present invention.

EXAMPLE 1

105.8 g of methyl 3-oxo-pentanoate (0.813 mol) are added to 1000 g of a toluene solution containing 128.0 g of 7-ethyl tryptophol (0.676 mol). The solution is brought to a temperature of approximately 0° C. Keeping this temperature, 74.0 g (2.029 mol) of gaseous hydrochloric acid dissolved in 20% by weight isobutyl alcohol are added drop by drop.

Once the addition is completed, the mixture is poured into a solution of 10% potassium bicarbonate, and the phases are separated. The organic phase is concentrated until 302 g of residue are obtained, which are then re-diluted and re-crystallised using 420.0 ml of methyl alcohol, to obtain 145.0 g of etodolac methyl ester with HPLC purity degree higher than or equal to 97.5%.

EXAMPLE 2

112 g of isobutyl alcohol and 41.3 g (0.3169 mol) of methyl 3-oxo-pentanoate are added to 469.4 g of a toluene solution containing 50.0 g of 7-ethyl tryptophol (0.2641 mol).

The solution is brought to a temperature comprised between 0 and 5° C. Keeping this temperature range, 80.9 g (0.7923 mol) of concentrated sulphuric acid (98%) are added drop by drop.

Once the addition is completed, the mixture is poured into a solution of 10% potassium bicarbonate, and the phases are separated. The organic phase is concentrated until 148.0 g of residue are obtained, which are then re-diluted and re-crystallised using 130.0 g of methyl alcohol, to obtain 40.5 g of raw etodolac methyl ester.

We claim:

1. In a process for the preparation of etodolac, comprising:

a) reacting 7-ethyl-tryptophol of formula (II)

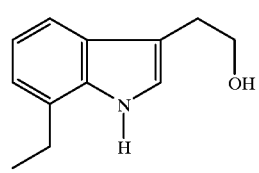

(II)

with methyl 3-oxo-pentanoate of formula (III) in an apolar solvent

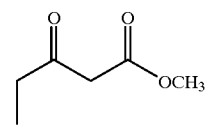

(III)

thereby obtaining the methyl 1,8-diethyl-1,3,4,9-tetrahydropyrano [3,4-bis] indole-1-acetate of formula (IV)

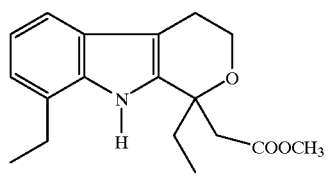

(IV)

b) subsequent hydrolysing of the intermediate compound of formula (IV) to etodolac (I),

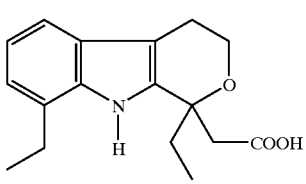

(I)

the improvement consisting of carrying out step (a) at temperatures comprised between −20° C. and +50° C. in the presence of a concentrated mineral acid, the molar ratio of said mineral acid to 7-ethyl-tryptophol being comprised between 0.5 and 5.

2. The process according to claim 1, wherein the inorganic mineral acid used in step (a) is selected from the group consisting of gaseous hydrochloric acid dissolved in a $C_1$–$C_5$ alcohol and concentrated sulphuric acid.

3. The process according to claim 2, wherein said alcohol is isobutanol and the concentration of hydrochloric acid in isobutanol is 20% by weight.

4. The process according to claim 1, wherein said molar ratio of mineral acid to 7-ethyl tryptophol is 3:1.

5. The process according to claim 2, wherein, when sulphuric acid is used as mineral acid in step (a), a $C_1$–$C_5$ alcohol is used as co-solvent.

6. The process according to claim 1, wherein step (a) is carried out at a temperature of 0° C.

7. The process according to claim 1, wherein the apolar solvent of step (a) is toluene.

8. The process according to claim 1, wherein the inorganic mineral acid used in step (a) is 20% by weight of gaseous hydrochloric acid dissolved in isobutanol; the molar ratio of inorganic mineral acid to 7-ethyl tryptophol is 3:1; and step (a) is carried out at a temperature of 0° C.

9. The process according to claim 1, wherein the inorganic mineral acid used in step (a) is sulfuric acid; the ratio of inorganic mineral acid to 7-ethyl tryptophol is 3:1; and step (a) is carried out at a temperature of 0° C.

* * * * *